United States Patent [19]

Angelone, Jr. et al.

[11] Patent Number: 5,587,153
[45] Date of Patent: Dec. 24, 1996

[54] CLEAR, GELLED ALUMINUM AND ZIRCONIUM SALT CONTAINING ANTIPERSPIRANT FORMULATION

[75] Inventors: Philip P. Angelone, Jr., Wilmington; Nancy M. Karassik, Concord; William R. Grace, Reading, all of Mass.

[73] Assignee: The Gillette Company, Boston, Mass.

[21] Appl. No.: 204,898

[22] Filed: Mar. 2, 1994

Related U.S. Application Data

[63] Continuation of Ser. No. 592,570, Oct. 4, 1990, abandoned.

[51] Int. Cl.$^6$ .............................. A61K 7/34; A61K 7/38
[52] U.S. Cl. ..................... 424/66; 424/68; 514/938
[58] Field of Search .................... 424/65, 66, 68; 514/938

[56] References Cited

U.S. PATENT DOCUMENTS

| | | | |
|---|---|---|---|
| 3,957,969 | 5/1976 | Fujiyama | 424/64 |
| 4,120,948 | 10/1978 | Shelton | 424/66 |
| 4,122,029 | 10/1978 | Gee | 514/938 X |
| 4,265,878 | 5/1981 | Keil | 424/68 |
| 4,268,499 | 5/1981 | Keil | 424/68 |
| 4,278,655 | 7/1981 | Elmi | 424/47 |
| 4,350,605 | 9/1982 | Hughett | 424/68 |
| 4,383,988 | 5/1983 | Tong | 424/68 |
| 4,673,570 | 6/1987 | Soldati | 424/68 |
| 4,708,863 | 11/1987 | Bews | 424/67 |
| 4,725,431 | 2/1988 | Hourihan | 424/68 |
| 4,782,095 | 11/1988 | Gum | 424/59 X |
| 4,944,938 | 7/1990 | Potini | 424/68 |
| 4,948,578 | 8/1990 | Burger et al. | 424/68 |
| 5,162,378 | 11/1992 | Guthauser | 514/785 |

FOREIGN PATENT DOCUMENTS

| | | |
|---|---|---|
| 291334 | 11/1988 | European Pat. Off. . |
| 0373499 | 6/1990 | European Pat. Off. . |
| 2618351 | 1/1989 | France . |
| 2079300 | 1/1982 | United Kingdom . |

OTHER PUBLICATIONS

Dow Corning, "Information About Cosmetic Ingredients", (1982).

"Deodorant & Antiperspirant Formulary", *Cosmetics and Toiletries*, vol. 100, pp. 65–75 (Dec., 1985).

Dow Corning, "Dow Corning Transparent Antiperspirant Gel Formulation 7635–113A". (no date available).

*Primary Examiner*—C. Warren Ivy
*Assistant Examiner*—Evelyn Huang
*Attorney, Agent, or Firm*—Fish & Richardson, P.C.

[57] ABSTRACT

A clear gel-type cosmetic product has a viscosity of at least about 50,000 cps at 21° C., and includes an emulsion with an oil phase and a water phase that includes an incorporated active ingredient. The refractive indices of the water and oil phases match to at least 0.0004, the refractive index of the product is about 1.4000, and the product clarity is better than thirty NTU.

33 Claims, No Drawings

CLEAR, GELLED ALUMINUM AND ZIRCONIUM SALT CONTAINING ANTIPERSPIRANT FORMULATION

This is a continuation of application Ser. No. 07/592,570, filed Oct. 4, 1990, now abandoned.

This invention relates to cosmetic products such as deodorants and antiperspirants and processes for forming such cosmetic products.

Antiperspirant and deodorant products are well-known in the cosmetic art. Deodorant and antiperspirant products may be in the form of an emulsion which includes a water phase and an oil phase. Gel-type emulsion deodorants and antiperspirants are used by rubbing an area of the body such as the underarm to apply a layer of the composition to the skin which reduces odor and/or perspiration. It is desirable that such products have aesthetic characteristics of non-crumbling, smoothness, non-oiliness and non-tackiness. Clarity of such products is a long-sought desirable aesthetic characteristic. Another desirable characteristic is that no readily visible residue as, e.g., a white layer, be left on the skin after the deodorant or antiperspirant is applied.

In accordance with one aspect of the invention, there is provided an optically clear cosmetic product with the ability of being packaged in a clear container, of the deodorant or antiperspirant type that has a refractive index of 1.3975–1.4025 at 21° C., an optical clarity better than fifty NTU (Nephelometric Turbidity Units) at 21° C. and a viscosity of at least about 50,000 cps at 21° C., and is an emulsion with an oil phase and a water phase with an active ingredient incorporated therein. The refractive indices ($\eta_D$) (measured at 5893Å) of the water and oil phases match to within 0.0004. An optically clear antiperspirant or deodorant product of the invention is one that is visually clear, and, like glass, allows ready viewing of objects behind it. By contrast, a translucent deodorant or antiperspirant product, although allowing light to pass through, causes the light to be so scattered that it will be difficult to see clearly objects behind the translucent product. Preferably, the product has a turbidity measurement of less than 30 NTU. Distilled water has a turbidity of 0 NTU and whole milk diluted one part in 350 parts of distilled water has a turbidity of 200 NTU. The turbidity measurements discussed hereinafter were made with a Orbeco-Hellige #965 Direct-Reading Turbidimeter.

The oil phase preferably makes up about ten to twenty-five percent of the product and includes an emulsifier which when properly mixed with the water phase components yields a water-in-oil emulsion. The oil phase is typically a blend of liquids and includes, a polyorganosiloxane, for example, dimethicone (e.g. Dow Corning DC-225 fluid, $\eta_D=1.3995$), isopropyl myristate ($\eta_d=1.4340$) isopropyl palmitate, ($\eta_D=1.4370$), or diisopropyl sebacate ($\eta_D=1.4320$), and a silicone emulsifying agent. A particularly suitable emulsifying agent is a polyether substituted silicone of Cyclomethicone [and] Dimethicone Copolyol ($\eta_D=1.3995$) (available as DC-3225C from Dow Corning). The DC-3225C emulsifier is useful for preparing stable water-in-silicone emulsions where silicone makes up a large portion of the oil phase, and is a dispersion of a silicone surfactant (dimethicone copolyol) (ten percent) in cyclomethicone (Dow Corning 344 Fluid) (ninety percent).

The water phase includes one or a combination of various polar species such as water ($\eta_D=1.3333$), propylene glycol ($\eta_D=1.4320$), sorbitol ($\eta_D=1.4611$) and ethanol ($\eta_D=1.3618$). The water phase includes, in solution, a deodorant and/or antiperspirant active ingredient such as Triclosan, Benzethonium Chloride and/or an astringent salt of aluminum or zirconium, such as aluminum chlorohydrate or aluminum zirconium tetrachlorohydrex-gly. Particularly preferred active ingredients are a fifty percent aqueous solution of aluminum chlorohydrate ($\eta_D$ of about 1.4070), Triclosan (Irgasan, DP-300, Ciba-Geigy—a 3% solution in ethanol has $\eta_D=1.3638$) and Benzethonium Chloride (Hyamine 1622 Rohn and Haas, a 2% solution in ethanol has $\eta_D=1.3638$). The active ingredient(s) should be present in an amount effective to reduce perspiration or odor, as the case may be, when applied to the skin. The precise amount of active component that can be used will vary with the particular component and formula. As a general rule, however, an antiperspirant product should contain anywhere from about ten to about thirty percent (more preferably about twenty percent to about thirty percent) of active antiperspirant component. A deodorant product should contain up to about 0.5 percent Triclosan, up to about 0.5 percent Benzethonium Chloride or up to about six percent aluminum chlorohydrate as the active deodorant component.

The product can also contain additional cosmetic ingredients such as emollients, colorants, fragrances, and preservatives. Percentages set out in the description and claims are in weight percent.

In preferred embodiments, the oil phase comprises about ten to about twenty-five percent by weight of the product, and the water phase generally makes up between about seventy-five to about ninety percent. To provide an optically clear antiperspirant or deodorant product, the refractive indices ($\eta_D$) of the oil and water phases are measured using a suitable refractometer such as a Reichert-Jung, Abbe Mark II Refractometer Model 10480, and one phase is adjusted as necessary to have a refractive index that matches that of the other phase within 0.0004.

In particular antiperspirant embodiments, the oil phase is formulated and its refractive index is optically measured; the water phase is formulated using a 50% aqueous aluminum chlorohydrate solution, propylene glycol, water and ethanol, and the refractive index of the water phase is optically measured. In a particular deodorant embodiment, the oil phase is formulated and its refractive index is measured. Propylene glycol, water, and ethanol are added to an aluminum chlorohydrate solution and mixed, and sorbitol is then added; and the refractive index of the water phase is then optically measured. In both antiperspirant and deodorant embodiments, propylene glycol or water is added to change the water phase refractive index so that it matches the refractive index ($\eta_D$) of the oil phase to at least 0.0004 at room temperature (20°–25° C.). Following the adjustment, the water phase is optically remeasured to verify the match. For example, for an oil phase with refractive index of 1.3997 and an initial water phase refractive index of 1.3985, propylene glycol is added to the water phase to produce a matching water phase refractive index of 1.3997. The water phase is then slowly added to the oil phase as the mixture is mixed at low speed; fragrance is then added; and the mixture is sheared to form a stable water in oil emulsion with viscosity in excess of 50,000 cps at 21° C. More preferably, the viscosity is between about 80,000–200,000 cps and most preferably around 140,000 cps. The following Examples 1–7 illustrate representative antiperspirant and deodorant products and are given by way of illustration only and are not to be considered as being limiting. The amounts in the Examples and the claims are in weight percent.

In the following Examples, the ingredients of the oil phase are combined and its refractive index at room temperature (about 21° C.) is measured. The water phase is then formulated, its refractive index is measured also at room temperature and adjusted as necessary to match that of the oil phase, and optically remeasured to verify the match. The water phase is then slowly added to the oil phase over about twenty minutes to slowly build viscosity while a mixing head is driven to maintain a mild vortex. Perfume is then added and the mixture is then sheared with a suitable homogenizing device to produce a gel with a viscosity of around 140,000 cps at 21° C.

EXAMPLE 1

(Antiperspirant)

| CFTA NAME | % ACTIVE |
|---|---|
| WATER PHASE | |
| WATER | 37.01 |
| ALUMINUM CHLOROHYDRATE | 30.00 |
| ETHANOL (SD ALCOHOL 40, 200 PROOF) | 10.00 |
| PROPYLENE GLYCOL | 4.99 |
| OIL PHASE | |
| DIMETHICONE (DC-225) | 9.85 |
| CYCLOMETHICONE & DIMETHICONE COPOLYOL (DC-3225C) | 8.00 |
| FRAGRANCE | |
| FRAGRANCE | 0.15 |

The oil phase had a refractive index of 1.3995 at 21.3° C.; the water phase had an initial refractive index of 1.3990 and the water phase refractive index was adjusted by the addition of propylene glycol so that the water phase refractive index matched the 1.3995 oil phase refractive index. The resulting composition of Example 1 had a viscosity of 146,000 cps, a measured turbidity of 22 NTU and a refractive index of 1.3998 at 21° C. and was an effective antiperspirant

EXAMPLE 2

(Antiperspirant)

| CFTA NAME | % ACTIVE |
|---|---|
| WATER PHASE | |
| WATER | 37.01 |
| ALUMINUM CHLOROHYDRATE | 30.00 |
| ETHANOL (SD ALCOHOL 40, 200 PROOF) | 10.00 |
| PROPYLENE GLYCOL | 4.99 |
| OIL PHASE | |
| DIMETHICONE | 10.00 |
| CYCLOMETHICONE & DIMETHICONE COPOLYOL | 8.00 |

The oil phase had a refractive index of 1.3998 at 20.7° C. and the water phase had a refractive index of 1.3996 at 20.8° C. Its refractive index was not adjusted. The resulting composition of Example 2 had a viscosity of 110,000 cps, a measured turbidity of 18 NTU and a refractive index of 1.3996 at 20.8° C., and was an effective antiperspirant.

EXAMPLE 3

(Antiperspirant)

| CFTA NAME | % ACTIVE |
|---|---|
| WATER PHASE | |
| WATER | 37.14 |
| ALUMINUM ZIRCONIUM TETRACHLORO-HYDREX-GLY | 20.00 |
| PROPYLENE GLYCOL | 14.86 |
| ETHANOL (SD ALCOHOL 40, 200 PROOF) | 10.00 |
| OIL PHASE | |
| CYCLOMETHICONE & DIMETHICONE COPOLYOL | 8.00 |
| DIMETHICONE | 10.00 |

The oil phase had a refractive index of 1.3992; the water phase had an initial refractive index of 1.4018 and the water phase refractive index was adjusted by the addition of water so that the water phase refractive index matched the 1.3992 oil phase refractive index. The resulting composition of Example 3 had a viscosity of 140,000 cps, a measured turbidity of 43 NTU, and a refractive index of 1.3992, and was an effective antiperspirant.

EXAMPLE 4

(Antiperspirant)

| CFTA NAME | % ACTIVE |
|---|---|
| WATER PHASE | |
| WATER | 37.010 |
| ALUMINUM CHLOROHYDRATE | 30.000 |
| ETHANOL (SD ALCOHOL 40, 200 PROOF) | 10.000 |
| PROPYLENE GLYCOL | 4.990 |
| OIL PHASE | |
| DIMETHICONE (DC-225) | 9.825 |
| CYCLOMETHICONE & DIMETHICONE COPOLYOL (DC-3225C) | 8.000 |
| FRAGRANCE | |
| FRAGRANCE | 0.175 |

The oil phase had a refractive index of 1.3997 at 21.0° C.; the water phase had an initial refractive index of 1.3985 at 20.9° C. and the water phase refractive index was adjusted by the addition of 0.5 kilogram of propylene glycol to the 49.3 kilogram water phase so that the water phase refractive index matched the 1.3997 oil phase refractive index. The resulting composition of Example 4 had a viscosity of 122,000 cps, a measured turbidity of 22 NTU, and a refractive index of 1.3997 at 20.7° C., and was an effective antiperspirant

EXAMPLE 5

(Antiperspirant)

| CFTA NAME | % ACTIVE |
|---|---|
| WATER PHASE | |
| WATER | 37.010 |
| ALUMINUM CHLOROHYDRATE | 30.000 |
| ETHANOL (SD ALCOHOL 40, 200 PROOF) | 10.000 |
| PROPYLENE GLYCOL | 4.990 |
| OIL PHASE | |
| DIMETHICONE (DC-225) | 9.825 |
| CYCLOMETHICONE & DIMETHICONE COPOLYOL (DC-3225C) | 8.000 |
| FRAGRANCE | |
| FRAGRANCE | 0.175 |

The oil phase had a refractive index of 1.3997 at 20.9° C.; the water phase had an initial refractive index of 1.3995 at 21.0° C. The water phase refractive index was adjusted with propylene glycol to produce a remeasured water phase refractive index of 1.3997 at 20.9° C. The resulting composition of Example 5 had a viscosity of 134,000 cps, a measured turbidity of 18 NTU, and a refractive index of 1.3997 at 20.9° C., and was an effective antiperspirant.

EXAMPLE 6

(Deodorant)

| CFTA NAME | % ACTIVE |
|---|---|
| WATER PHASE | |
| WATER | 33.25 |
| SORBITOL | 14.00 |
| ETHANOL (SD ALCOHOL 40, 200 PROOF) | 12.00 |
| PROPYLENE GLYCOL | 22.50 |
| TRICLOSAN | 0.25 |
| SODIUM HYDROXIDE | 0.02 |
| OIL PHASE | |
| DIMETHICONE (DC-225) | 9.70 |
| CYCLOMETHICONE & DIMETHICONE COPOLYOL (DC-3225C) | 8.00 |
| FRAGRANCE | |
| FRAGRANCE | 0.30 |

The oil phase had a refractive index of 1.4001 at 19.8° C.; the water phase had an initial refractive index of 1.3998 and its refractive index was adjusted by the addition of propylene glycol to match the 1.4001 oil phase refractive index. The resulting composition of Example 6 had a viscosity of 168,000 cps, a measured turbidity of 26 NTU, and a refractive index of 1.3999 at 24° C., and was an effective deodorant.

EXAMPLE 7

(Deodorant)

| CFTA NAME | % ACTIVE |
|---|---|
| WATER PHASE | |
| WATER | 35.00 |
| SORBITOL | 14.00 |
| ALUMINUM CHLOROHYDRATE | 3.00 |
| ETHANOL (SD ALCOHOL 40, 200 PROOF) | 10.00 |
| PROPYLENE GLYCOL | 20.00 |
| OIL PHASE | |
| DIMETHICONE (DC-225) | 9.70 |
| CYCLOMETHICONE & DIMETHICONE COPOLYOL (DC-3225C) | 8.00 |
| FRAGRANCE | |
| FRAGRANCE | 0.30 |

The oil phase had a refractive index of 1.3998 at 20.3° C.; the water phase had an initial refractive index of 1.3991 and the water phase refractive index was adjusted by the addition of 0.15 kilogram of propylene glycol to the 49.4 kilogram water phase so that the water phase refractive index matched the 1.3998 oil phase refractive index. The resulting deodorant composition of Example 7 had a viscosity of 160,000 cps, a measured turbidity of 23 NTU, and a refractive index of 1.3997 at 24° C., and was an effective deodorant.

While particular embodiments of the invention has been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. An optically clear deodorant or antiperspirant product, comprising: a water-in-oil emulsion, said emulsion being a gel having a viscosity between about 50,000 cps and about 200,000 cps at 21° C. and a refractive index ($n_D$) in the range of 1.3975–1.4025, said emulsion having a water phase that makes up between seventy-five to ninety percent of said emulsion, with a deodorant or antiperspirant effective salt of aluminum and zirconium dissolved in said water phase and an oil phase.

2. The product of claim 1 wherein the clarity of said product is better than fifty NTU at 21° C.

3. The product of claim 1 wherein a principal constituent of said oil phase is a silicone.

4. The product of claim 1 wherein said oil phase includes a silicone with a viscosity of less than fifty cps at 21° C. and said oil phase makes up at least about ten percent of said emulsion.

5. The product of claim 1 wherein said salt comprises aluminum-zirconium tetrachlorohydrex-gly.

6. The product of claim 1 wherein said product has a viscosity of at least about 80,000 cps at 21° C.

7. The product of claim 1 wherein said water phase includes water, propylene glycol and ethanol.

8. The product of claim 7 wherein said water phase further includes sorbitol.

9. The product of claim 1 further including fragrance.

10. The product of claim 1 and further including a container with an optically clear wall in which said product is housed.

11. The product of claim 2 wherein said product has a viscosity between about 80,000–200,000 cps at 21° C.; said oil phase makes up at least about ten percent of said emulsion; said water phase includes water, propylene glycol and ethanol; and said oil phase comprises a silicone.

12. The product of claim 11 wherein said water phase includes about thirty-seven percent water, about twenty percent aluminum-zirconium tetrachlorohydrex-gly, about ten percent ethanol, and about fifteen percent propylene glycol; and said oil phase includes about ten percent dimethicone and about eight percent of an emulsifier comprising cyclomethicone and dimethicone copolyol.

13. The product of claim 12 wherein said product has a refractive index of about 1.3992 at 21° C., a measured turbidity of about forty-three NTU at 21° C. and a viscosity at 21° C. of about 140,000 cps.

14. An optically clear deodorant or antiperspirant product, comprising:

a water-in-oil emulsion, said emulsion being a gel having a viscosity of at least 50,000 cps at 21° C. and having:

(a) a water phase comprising seventy-five to ninety percent of said emulsion, said water phase having dissolved therein a deodorant or antiperspirant effective salt of aluminum and zirconium and (b) an oil phase comprising ten to twenty-five percent of said emulsion and including a silicone and a polyether substituted silicone emulsifying agent.

15. A method of producing an optically clear deodorant or antiperspirant product, comprising:

providing an oil phase, optically determining the refractive index of said oil phase, providing a water phase having dissolved therein a deodorant or antiperspirant effective salt of aluminum and zirconium, optically determining the refractive index of said water phase, adjusting the refractive index of at least one of said oil and water phases, if necessary, to match to at least 0.0004 at room temperature;

optically redetermining the refractive index of said adjusted one phase to verify said match;

mixing said oil and water phases; and further processing said mixture of said oil and water phases to produce a water-in-oil emulsion, said emulsion being a gel having a viscosity of between about 50,000 cps to 200,000 cps at 21° C.

16. The method of claim 15 and further including the steps of adding perfume to said mixture.

17. The method of claim 15 wherein the refractive index of said water phase is adjusted after its refractive index is optically determined in order to match the refractive index of said oil phase.

18. The method of claim 17 wherein said water phase includes water, propylene glycol and ethanol.

19. The method of claim 18 wherein said water phase comprises about seventy-five to ninety percent of said emulsion.

20. The method of claim 19 wherein said oil phase has an optically measured refractive index in the range of 1.3975 to 1.4025 at 21° C.

21. The method of claim 16 wherein a principal constituent of said oil phase is silicone, said oil phase is selected from one or a combination of a polyether substituted silicone emulsifier, dimethicone, isopropyl myristate, isopropyl palmitate, and diisopropyl sebacate.

22. The method of claim 21 wherein said further processing provides a viscosity of said product between about 80,000 and 200,000 cps at 21° C.

23. The product of claim 12 and further including a container with an optically clear wall in which said product is housed.

24. The product of claim 14 and further including a container with an optically clear wall in which said product is housed.

25. An optically clear antiperspirant or deodorant product comprising a water-in-oil emulsion with a viscosity between 50,000 to 200,000 cps at 21° C., said emulsion being a gel having a refractive index ($n_D$) in the range of 1.3975–1.4025, and a clarity better than 50 NTU at 21° C. said emulsion having a water phase that makes up between seventy-five percent and ninety percent of said emulsion and includes an antiperspirant or deodorant effective salt of aluminum and zirconium dissolved in said water phase, and an oil phase which makes up between ten percent and twenty-five percent of said emulsion and includes a silicone and a polyether-substituted silicone emulsifying agent, wherein the refractive index of the water phase matches the refractive index of the oil phase to at least 0.0004.

26. The product of claim 25 wherein the silicone is dimethicone and the polyether-substituted silicone emulsifying agent is cyclomethicone and dimethicone copolyol.

27. The product of claim 26 having a clarity better than 30 NTU and a viscosity between 80,000 to 200,000 cps at 21° C.

28. The product of claim 27 wherein, the water phase additionally includes propylene glycol, ethanol and optionally sorbitol.

29. The method of claim 15 wherein said water-in-oil emulsion has a clarity of better than fifty NTU at 21° C. and a refractive index ($n_D$) in the range of 1.3975–1.4025.

30. The product of claim 14 wherein the silicone is dimethicone and the polyether-substituted silicone emulsifying agent is cyclomethicone and dimethicone copolyol.

31. The product of claim 14 or 30 wherein the clarity of said product is better than 50 NTU at 21° C.

32. The product of claim 31 wherein said product has a viscosity between 80,000 and 200,000 cps at 21° C.

33. The product of claim 32 wherein the water phase additionally includes propylene glycol and ethanol.

* * * * *